US008134005B2

(12) United States Patent
Knochel et al.

(10) Patent No.: US 8,134,005 B2
(45) Date of Patent: Mar. 13, 2012

(54) PREPARATION AND USE OF MAGNESIUM AMIDES

(75) Inventors: Paul Knochel, Munich (DE); Arkady Krasovskiy, Midland, MI (US); Valeria Krasovskaya, Midland, MI (US); Christoph Josef Rohbogner, Feldolling (DE); Giuliano Cesar Clososki, Curltlba (BR)

(73) Assignee: Ludwig-Maximilians-Universitat München, München (DE)

( * ) Notice: Subject to any disclaimer, the term of this patent is extended or adjusted under 35 U.S.C. 154(b) by 736 days.

(21) Appl. No.: 12/087,351

(22) PCT Filed: Jan. 18, 2007

(86) PCT No.: PCT/EP2007/050492
§ 371 (c)(1),
(2), (4) Date: Nov. 17, 2008

(87) PCT Pub. No.: WO2007/082911
PCT Pub. Date: Jul. 26, 2007

(65) Prior Publication Data
US 2009/0176988 A1 Jul. 9, 2009

(30) Foreign Application Priority Data

Jan. 18, 2006 (EP) .................................... 06001017

(51) Int. Cl.
C07D 295/027 (2006.01)
C07D 207/00 (2006.01)
C07F 7/02 (2006.01)
C07C 211/01 (2006.01)
(52) U.S. Cl. ......... 546/184; 548/400; 556/412; 564/463
(58) Field of Classification Search .................. None
See application file for complete search history.

(56) References Cited

U.S. PATENT DOCUMENTS

| 4,944,894 | A | * | 7/1990 | Mehta et al. ............. 252/182.12 |
| 5,002,689 | A | | 3/1991 | Mehta et al. |
| 5,300,252 | A | * | 4/1994 | Morrison ................... 252/182.3 |
| 5,320,774 | A | | 6/1994 | Mehta et al. |

FOREIGN PATENT DOCUMENTS

| DE | 39 05 857 A1 | 9/1989 |
| WO | WO2007/082911 | 7/2007 |

OTHER PUBLICATIONS

Boudet, Nadege et al., "Mild Iodine-Magnesium Exchange of Iodoaromatics Bearing a Pyrimidine Ring with Isopropylmagnesium Chloride," Organic Letters, vol. 9, No. 26 pp. 5525-5528 (2007).
Clososki et al., "Direct Magnesiation of Polyfunctionalized Arenes and Heteroarenes Using (tmp)$_2$Mg•2 LiCl," Angewandte Chemie, International Edition, vol. 46, No. 40, pp. 7681-7684 (2007).
International Preliminary Report on Patentability corresponding to International Application No. PCT/EP2008/050066 dated Jul. 21, 2009.

* cited by examiner

*Primary Examiner* — Brian J Davis
(74) *Attorney, Agent, or Firm* — Jenkins, Wilson, Taylor & Hunt, P.A.

(57) ABSTRACT

The present application relates to mixed Mg/Li amides of the general formula R1R2N—Mg(NR3R4)mX,.m zLiY (II) wherein $R^1$, $R^2$, $R^3$, and $R^4$ are, independently, selected from H, substituted or unsubstituted aryl or heteroaryl containing one or more heteroatoms, linear, branched or cyclic, substituted or unsubstituted alkyl, alkenyl, alkynyl, or silyl derivatives thereof; and $R^1$ and $R^2$ together, or $R^3$ and $R^4$ together can be part of a cyclic or polymeric structure; and wherein at least one of $R^1$ and $R^2$ and at least one of $R^3$ and R is other than H; X and Y are, independently, selected from the group consisting of F; Cl; Br; I; CN; SCN; NCO; HalO$_n$, wherein n=3 or 4 and Hal is selected from Cl, Br and I; NO$_3$; BF$_4$; PF$_6$; H; a carboxylate of the general formula $R^xCO_2$; an alcoholate of the general formula ORX; a thiolate of the general formula SR$^X$; R$^X$P(O)O$_2$; or SCOR$^X$; or SCSR$^X$; O$_n$SR$^x$, wherein n=2 or 3; or NO$_n$, wherein n=2 or 3; and a derivative thereof; wherein R$^x$ is a substituted or unsubstituted aryl or heteroaryl containing one or more heteroatoms, linear, branched or cyclic, substituted or unsubstituted alkyl, alkenyl, alkynyl, or derivatives thereof, or H; m is O or 1; and z>O; as well as a process for the preparation of the mixed Mg/Li amides and the use of these amides, e.g. as bases.

27 Claims, No Drawings

PREPARATION AND USE OF MAGNESIUM AMIDES

The present application relates to magnesium amides, a method for the preparation of magnesium amides and the use of these amides.

The metalation of aromatics is one of the most useful transformations in organic synthesis since it allows the regioselective functionalization of various aryl derivatives.[1] Traditionally, strong bases such as alkyl lithium (RLi) or lithium amides ($R_2$NLi) have been used to perform such deprotonations. However, these highly reactive bases display often undesirable side reactions due to the too high reactivity of the resulting aryl lithium compounds. Another serious limitation is the low stability of lithium amides in THF solutions at room temperature which requires an in situ generation of these reagents. Furthermore, the deprotonation of aromatics by lithium bases often requires very low temperatures (−78° C. to −90° C.) which complicates the scale-up of these reactions and the use of solvent mixtures such as THF/pentane may be needed.

Alternative methods have been developed using magnesium amides[2] such as compounds 1-3 or amido zincates[3] 4 (see Scheme 1). The low solubility of the magnesium amides $R_2$NMgCl (1) could be improved by Eaton who developed the use of magnesium amides of type $R_2$NMgR' (2) and $(R_2N)_2$Mg (3). Nevertheless, for achieving high conversions it is usually necessary to use a large excess of the magnesium amides (2-8 equivalents), which complicates further quenching reactions with electrophiles (up to 15 equivalents of electrophile may have to be used). Similarly, the dialkyl amino zincate 4 requires the use of 3.5-4 equivalents of an electrophile in subsequent quenching reactions.

Scheme 1. Typical bases used for the deprotonation of aromatics or heterocycles.

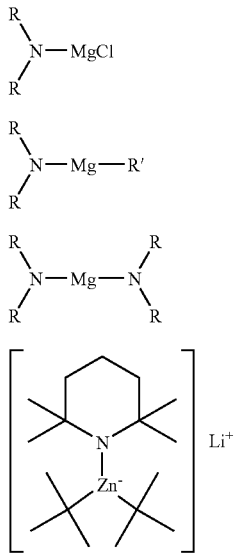

The use of these bases is thus either limited by their poor solubility, or they are not very efficient in view of the amounts of base and the amount of electrophile needed to perform the desired conversion. Their activity or reactivity is very low.

The use of lithium salts to increase the solubility of Grignard reagents is known from EP 1 582 523. In this application, the main function of the Grignard reagents of the general formula $R*(MgX)_nLiY$ disclosed therein is to perform a halogen/magnesium exchange in either aliphatic or aromatic systems. The Grignard reagent derivatives provide a "nucleophilic carbon atom" at a magnesium-carbon-bond. By the addition of a lithium salt to the Grignard reagent, the reactivity of the Grignard reagents can be increased by forming a magnesiate intermediate. These Grignard reagents then show a higher reactivity and selectivity due to the formation of a magnesiate intermediate.

It is an object of the present invention to provide an inexpensive magnesium base which is highly soluble and more reactive. A further object of the present invention is to provide a magnesium base showing a high kinetic activity and a high selectivity.

These objects are achieved by the features of the independent claims. Preferred embodiments are set forth in the dependent claims.

Surprisingly, the inventors found that mixed magnesium and lithium amides of type $R^1R^2N$—MgX zLiY (I) can be prepared by reacting an amine $R^1R^2$NH with a Grignard reagent R'MgX in the presence of LiY or with R'MgX zLiY in a solvent.

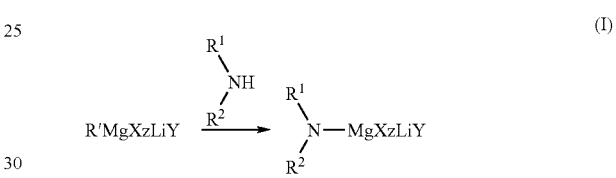

(I)

$R^1$, $R^2$ and R' independently are selected from substituted or unsubstituted aryl or heteroaryl containing one or more heteroatoms, linear, branched or cyclic, substituted or unsubstituted alkyl, alkenyl, alkynyl, or derivatives thereof, and, for $R^1$ and $R^2$ only, the silyl derivatives thereof. One of $R^1$ and $R^2$ may be H; or $R^1$ and $R^2$ together can be part of a cyclic or polymeric structure.

X and Y independently are selected from the group consisting of F; Cl; Br; I; CN; SCN; NCO; $HalO_n$, wherein n=3 or 4 and Hal is selected from Cl, Br and I; $NO_3$; $BF_4$; $PF_6$; H; a carboxylate of the general formula $R^XCO_2$; an alcoholate of the general formula $OR^X$; a thiolate of the general formula $SR^X$; $R^XP(O)O_2$; or $SCOR^X$; $O_nSR^X$, wherein n=2 or 3; or $NO_n$, wherein n=2 or 3; and a derivative thereof, wherein Rx is a substituted or unsubstituted aryl or heteroaryl containing one or more heteroatoms; linear, branched or cyclic, substituted or unsubstituted alkyl, alkenyl, alkynyl, or derivatives thereof, or H.

X and Y may be identical or different. In the above given context, z>0.

The amides of formula I can also be prepared in an alternative way by reacting a lithium amide of the formula $R^1R^2$NLi with a magnesium salt of the form $MgX_2$ or Mg XY. This reaction is preferably carried out in a solvent. In order to achieve a compound of formula I, the magnesium salt and the lithium amide are reacted in approximately equimolar ratio. Thus, the ratio of lithium amide to magnesium salt is usually in the range of 1:0.8-1.2, preferably in the range of 1:0.9-1.1, and most preferably in the range of 1:0.95-1.05.

Additionally, the inventors found that magnesium bisamides of the general formula

(II)

can be prepared. In this formula, $R^1$, $R^2$, $R^3$, and $R^4$ are, independently, selected from H, substituted or unsubstituted aryl or heteroaryl containing one or more heteroatoms, linear, branched or cyclic, substituted or unsubstituted alkyl, alkenyl, alkynyl, or silyl derivatives thereof, and $R^1$ and $R^2$ together, and/or $R^3$ and $R^4$ together can be part of a cyclic or polymeric structure; and wherein at least one of $R^1$ and $R^2$ and at least one of $R^3$ and $R^4$ is other than H.

X and Y are, independently, selected from the group consisting of F; Cl; Br; I; CN; SCN; NCO; $HalO_n$, wherein n=3 or 4 and Hal is selected from Cl, Br and I; $NO_3$; $BF_4$; $PF_6$; H; a carboxylate of the general formula $R^XCO_2$; an alcoholate of the general formula $OR^X$; a thiolate of the general formula $SR^X$; $R^XP(O)O_2$; or $SCOR^X$; or $SCSR^X$; $O_nSR^X$, wherein n=2 or 3; or $NO_n$, wherein n=2 or 3; and a derivative thereof, wherein Rx is a substituted or unsubstituted aryl or heteroaryl containing one or more heteroatoms, linear, branched or cyclic, substituted or unsubstituted alkyl, alkenyl, alkynyl, or derivatives thereof, or H;

In the above given formula II, m is 0 or 1; and z>0. For m=0, the compounds of formula II are identical to the compounds of formula I. The adduct with a solvent should also be encompassed by any of the compounds of formula I or II.

The bisamides of the general formula II wherein m=1 can be prepared from the monoamides of formula I. When reacting $R^1R^2N$—MgX zLiY with $R^3R^4NLi$, a bisamide of formula II is formed. This reaction is equivalent to a reaction of a generally known Grignard reagent R'MgX in the presence of an amine $R^1R^2NH$, and subsequently with $R^3R^4NLi$. The lithium may also be added as a lithium salt in the form LiY, especially when the Grignard reagent or the monoamide are not complexed with a lithium salt. Obviously, the reagent may also be of the form $R^1R^2N$—MgX zLiY, wherein a lithium salt is already present with the monoamide. In this way, bisamides may be prepared, wherein the two amides are different. However, the two amides may also be the same.

Alternatively, the bisamides may be prepared by reacting two lithium amides $R^1R^2NLi$ and $R^3R^4NLi$ with a magnesium salt $MgX_2$. If both lithium amides are identical, or a magnesium monoamide is reacted with a lithium amide of the same type, a bisamide of the general formula $Mg(NR^1R^2)_2$ zLiY will result. For a higher solubility of the magnesium salt $MgX_2$, this salt may be prepared in situ, for example as described below.

Both the monoamides as well as the bisamides of the present invention show an increased solubility and a high reactivity. Unlike Grignard reagents, which can perform halogen/magnesium exchanges, the amides of the present invention are bases which will tolerate many functional groups, especially halogen substituents. This is due to the different nature of the nitrogen magnesium bond present in the amides of the present application in view of a carbon magnesium bond as in Grignard reagents. The increase in reactivity of the Grignard reagents in the presence of a lithium salt is due to the formation of magnesiate intermediates. In contrast thereto, however, the lithium salt which is added to the amides according to the present application prevents the formation of aggregates. The formation of aggregates is a well known problem in the background art in relation to magnesium amides. As a consequence, the amides known so far have to be used in high excess as they are not very reactive. As the amides of the present invention are not present as aggregates due to the presence of a lithium salt, the amides are much more reactive and more soluble than the amides known so far.

Many common solvents can be used in the present invention. In principle, any solvent capable of dissolving the specific amine and the Grignard reagent used as starting materials and the resulting products. In a preferred embodiment of the present invention, the solvent is selected from cyclic, linear or branched mono or polyethers, thioethers, amines, phosphines, and derivatives thereof containing one or more additional heteroatoms selected from O, N, S and P, preferably tetrahydrofuran (THF), 2-methyltetrahydrofuran, dibutyl ether, diethyl ether, tert-butylmethyl ether, dimethoxyethane, dioxanes, preferably 1,4-dioxane, triethylamine, ethyldiisopropylamine, dimethylsulfide, dibutylsulfide; cyclic amides, preferably N-methyl-2-pyrrolidone (NMP), N-ethyl-2-pyrrolidone (NEP), N-butyl-2-pyrrolidone (NBP); cyclic, linear or branched alkanes and/or alkenes wherein one or more hydrogens are replaced by a halogen, preferably dichloromethane, 1,2-dichloroethane, $CCl_4$; urea derivatives, preferably N,N'-dimethylpropyleneurea (DMPU); aromatic, heteroaromatic or aliphatic hydrocarbons, preferably benzene, toluene, xylene, pyridine, pentane, cyclohexane, hexane, heptane; hexamethylphosphorus triamide (HMPA), $CS_2$; or combinations thereof.

The process of the invention for the preparation of amides of formula I is carried out by reacting an amine $R^1R^2NH$ with a Grignard reagent R'MgX in the presence of LiY or with R'MgX zLiY in a solvent. The materials are contacted preferably at room temperature for the minimum time necessary to provide the desired yield. Temperatures between 0° C. and 50° C. are preferred, however, higher or lower reaction temperatures are also suitable. The preparation of the bisamides of formula II is usually carried out at temperatures between −40° C. and 50° C., preferably in the range of −20° C. to 30° C. and most preferred at around 0° C. A person skilled in the art will however be able to select a suitable temperature for the preparation of the amides of formula I or II by routine experimentation.

In another preferred embodiment, X and Y are independently or both Cl, Br or I, and preferably Cl.

In yet another preferred embodiment, the preparation of a compound a formula I is achieved by iPrMgCl LiCl[5]. This embodiment is particularly preferred since iPrMgCl LiCl is commercially available.

Generally, any Grignard reagent can be used to prepare the mixed Mg/Li-amides in the presence of any lithium salt. It is nevertheless preferred to use a Grignard reagent the side or by-products of which can easily be removed from the reaction mixture. The presence of a lithium salt accelerates the exchange reaction compared to homoleptic reagents RMgX and $R_2Mg$ without the use of a lithium salt.

According to a second aspect, the present invention is directed to the mixed Mg/Li amide $R^1R^2N$—MgX zLiY (I), wherein $R^1$, $R^2$, X, Y and z are defined as above. This corresponds to an amide according to formula II, wherein m=0. The second aspect also relates to a mixed Mg/Li bisamide of the general formula $R^1R^2N$—$Mg(NR^3R^4)_mX_{1-m}$zLiY (II), wherein $R^1$, $R^2$, $R^3$, $R^4$, X, Y, m and z are defined as above. It is to be understood that the adduct of a solvent is also comprised by any of these formulae.

A third aspect of the present invention is directed to a solution of the amide (I) or (II) in a solvent. The solvent can be any suitable solvent capable of dissolving the amide. Especially preferred solvents are the solvents listed above for the preparation of the amides.

All aspects and features described above in relation to the first aspect shall also apply to the second and third aspect of the invention.

In a fourth aspect, the present invention is related to the use of mixed Mg/Li amides (I) and (II). The amides of the present invention can be used to remove acidic protons. The deprotonated species can then subsequently be quenched with an electrophile. In principle it is possible to use all kinds of electrophiles that are, for example, cited in the following references, but are not limited thereto:
a) Handbook of Grignard reagents; edited by Gary S. Silverman and Philip E. Rakita (Chemical industries; v. 64).
b) Grignard reagents New Developments; edited by Herman G. Richey, Jr., 2000, John Wiley & Sons Ltd.
c) Methoden der Organischen Chemie, Houben-Weyl, Band XIII/2a, Metallorganische Verbindungen Be, Mg, Ca, Sr, Ba, Zn, Cd. 1973.
d) The chemistry of the metal-carbon bond, vol 4. edited by Frank R. Hartley. 1987, John Wiley & Sons.

The final aspect of the invention relates to the product of the reaction of an electrophile with a substrate which has been deprotonated with a reagent of the general formula I or II.

In all aspects relating to the monoamides of the formula I, z is preferably in the range from 0.01-5, more preferably from 0.5-2, even more preferably from 0.9 to 1.2 and most preferred about 1. In the most preferred embodiment of the invention according to formula I, z is used in an equimolar ratio compared to the amide.

In relation to the bisamide of formula II, wherein m=1, z is preferably in the range of from 0.01-5, more preferably from 0.5-2.5, even more preferably from 1.8 to 2.2 and most preferred about 2.

The present invention is described in the following on the basis of specific examples. Especially, i-PrMgCl is used as Grignard reagent. However, it is to be understood that the present invention is not limited to such examples.

Unless otherwise defined, all technical and scientific terms used herein have the same meaning as commonly understood by one of ordinary skill in the art to which this invention belongs. All publications and other references mentioned herein are incorporated by reference in their entirety.

As used herein, the terms "alkyl", "alkenyl" and "alkynyl" refer to linear, cyclic and branched, substituted and unsubstituted $C_1$-$C_{20}$ compounds. Preferred ranges for these compounds are $C_1$-$C_{10}$, preferably $C_1$-$C_5$ (lower alkyl) and $C_2$-$C_{10}$ and preferably $C_2$-$C_5$, respectively, for alkenyl and alkynyl. The term "cycloalkyl" generally refers to linear and branched, substituted and unsubstituted $C_3$-$C_{20}$ cycloalkanes. Here, preferred ranges are $C_3$-$C_{15}$, more preferably $C_3$-$C_8$.

Whenever any of the residues $R^1$, $R^2$, $R^3$ and/or $R^4$ are substituted by a substituent, the substituent may be selected by a person skilled in the art from any known substituent. A person skilled in the art will select a possible substituent according to his knowledge and will be able to select a substituent which will not interfere with other substituents present in the molecule and which will not interfere or disturb possible reactions, especially the reactions described within this application. Possible substituents include without limitation halogenes, preferably fluorine, chlorine, bromine and iodine;
aliphatic, alicyclic, aromatic or heteroaromatic hydrocarbons, especially alkanes, alkylenes, arylenes, alkylidenes, arylidenes, heteroarylenes and heteroarylidenes; carbonxylic acids including the salts thereof;
carboxylic acid halides;
aliphatic, alicyclic, aromatic or heteroaromatic carboxylilc acid esters;
aldehydes;
aliphatic, alicyclic, aromatic or heteroaromatic ketones;
alcohols and alcoholates, including a hydroxyl group;
phenoles and phenolates;
aliphatic, alicyclic, aromatic or heteroaromatic ethers;
aliphatic, alicyclic, aromatic or heteroaromatic peroxides;
hydroperoxides;
aliphatic, alicyclic, aromatic or heteroaromatic amides or amidines;
nitriles;
aliphatic, alicyclic, aromatic or heteroaromatic amines;
aliphatic, alicyclic, aromatic or heteroaromatic imines;
aliphatic, alicyclic, aromatic or heteroaromatic sulfides including a thiol group;
sulfonic acids including the salts thereof;
thioles and thiolates;
phosphonic acids including the salts thereof;
phosphinic acids including the salts thereof;
phosphorous acids including the salts thereof;
phosphinous acids including the salts thereof;

The substituents may be bound to the residues $R^1$, $R^2$, $R^3$ and/or $R^4$ via a carbon atom, an oxygen atom, a nitrogen atom, a sulfur atom, or a phosphorus atom. The hetero atoms in any structure containing hetero atoms, as e.g. heteroarylenes or heteroaromatics, may preferably be N, O, S and P.

When $R^1$ and $R^2$, or $R^3$ and $R^4$ can be part of a cyclic structure, it is to be understood that $R^1$ and $R^2$ together, or $R^3$ and $R^4$ together, are a divalent saturated or unsaturated, linear or branched alkyl, alkenyl or alkynyl which forms in connection with the nitrogen atom of the amide a cyclic secondary amide. An example of such a cyclic amide is the amide of TMPH. Further, the residues $R^1$ and $R^2$, and/or $R^3$ and $R^4$ can be part of a polymeric structure. The nitrogen atom of the amide is the connected to a polymeric backbone which may even contain more than one nitrogen atom for the formation of an amide according to the invention.

The term "aryl" as used herein refers to substituted or unsubstituted $C_4$-$C_{24}$ aryl. By "heteroaryl", a substituted or unsubstituted $C_3$-$C_{24}$ aryl, containing one or more heteroatoms as B, O, N, S, Se, P, is meant. Preferred ranges for both are $C_4$-$C_{15}$, more preferably $C_4$-$C_{10}$ and includes aryls and fused aryls with or without heteroatoms. A preferred ring size comprises 5 or 6 ring atoms.

Mixed magnesium and lithium amides $R^1R^2$NMgCl LiCl ($R^1$ and $R^2$=i-Pr or $R^1R^2$N=2,2,6,6-tetramethylpiperidyl) can be prepared by reacting i-PrMgCl LiCl[4,5] with diisopropylamine or 2,2,6,6-tetramethylpiperidine (TMPH), respectively, in THF (−20° C.-80° C., for 0.1-48 h). The resulting Li/Mg-reagents 5a ($R^1$ and $R^2$=i-Pr) and 5b ($R^1R^2$N=2,2,6,6-tetramethylpiperidyl) proved to have an excellent solubility in THF (0.6 M and 1.2 M, respectively) as well as an improved kinetic acidity and regioselectivity for the magnesation of various aromatics and heterocycles.

The activity of the amides (I) can be shown on the basis of the magnesiation of isoquinoline. Diisopropylamido magnesium chloride-lithium chloride 5a leads to the magnesiated isoquinoline 6 after 12 h reaction time at 25° C. and by using 2 equivalents of the base. After iodolysis, the iodoisoquinoline 7a is isolated in 88% yield (Scheme 2). Even more active is the sterically more hindered and less aggregated 2,2,6,6-tetramethylpiperidino magnesium chloride-lithium chloride reagent 5b. It leads to a complete magnesiation within 2 h at 25° C. Remarkably, with this base only 1.1 equivalents are required to achieve a complete metalation. The resulting Grignard reagent 6 provides after iodolysis the iodoisoquinoline 7a in 96% yield (Scheme 2 and Table 1).

Scheme 2. Magnesiation of isoquinoline

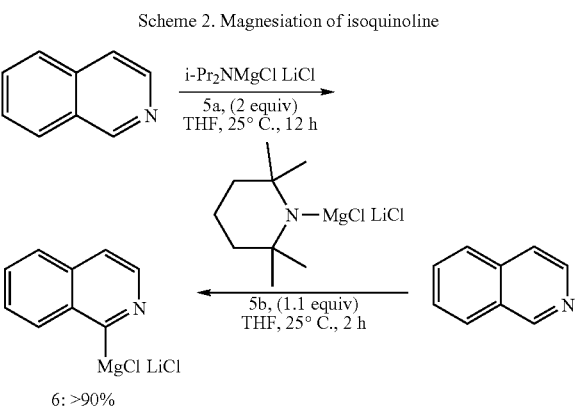

6: >90%

Scheme 3. Regioselective magnesiation of pyrimidines

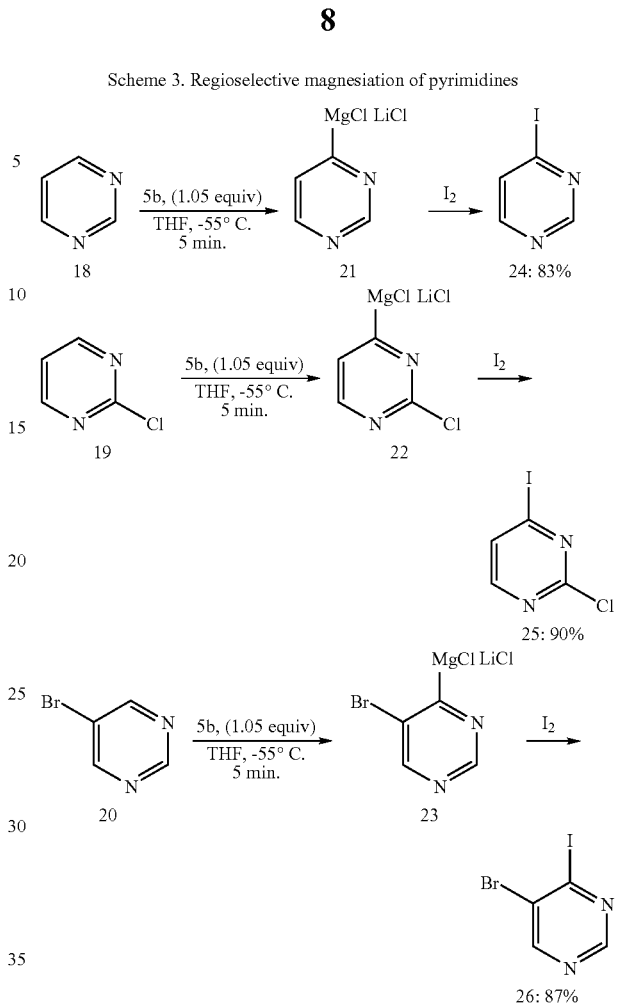

After the magnesation of a reagent, it can be subjected to a transmetalation. After e.g. a transmetalation with CuCN 2LiCl (20 mol %), the addition of benzoyl chloride (1.2 equiv.) provides the ketone 7b in 86% yield (entry 2 of Table 1).

The presence of an excess of magnesium amides often hampers the performance of palladium-catalyzed cross-couplings. The inventors found that the Grignard reagents generated by deprotonation with 5b (1.1 equiv.) such as 6 are readily transmetalated to the corresponding zinc derivative ($ZnCl_2$ (1.1 equiv.), 0° C., 5 min.) and undergo a Negishi— cross-coupling reaction using $Pd(dba)_2$ (5 mol %) (dba=dibenzylideneacetone), P(2-fur)$_3$ (7 mol %) (fur=furyl) with ethyl 4-iodobenzoate (1.2 equiv.; 50° C., 12 h) leading to the arylated quinoline (7c) in 82% yield. This behaviour is general and 3-bromoquinoline is metalated with 5b (1.1 equiv., −30° C., 0.5 h) leading to the 2-magnesiated quinoline 8 (entries 4 and 5 of Table 1). Thus, the quenching of 8 with $I_2$ and N,N-dimethylformamide (DMF) provides the two quinolines 9a and 9b in 96-93% yield.

Whereas the deprotonation of 2,6-dichloropyridine with i-Pr$_2$NMgCl LiCl 5a and lithium diisopropylamide (LDA)[8] provides a 1:1 mixture of 3- and 4-magnesiated 2,6-dichloropyridine, the use of TMPMgCl LiCl 5b furnishes only the 4-magnesiated pyridine 10. Its reaction with typical electrophiles ($I_2$, DMF and PhCHO) provides the expected products 11a-c in 84-93% yield (entries 6-8 of Table 1). Interestingly, metalation of 3,5-dibromopyridine with LDA proceeds selectively at 4-position[6b] while in the case of (TMPMgCl LiCl 5b 1.1 equiv, −20° C., 0.5 h) regioselective metalation of 3,5-dibromopyridine is observed leading after the reaction with DMF to the pyridylaldehyde 13 in 95% yield (entry 9 of Table 1).

The magnesiation of heterocycles bearing more acidic protons[7] such as thiazole, thiophene, furan, benzothiophene or benzothiazole proceeds smoothly between 0° C. and 25° C. leading to the organomagnesium derivatives 14a-c and 16a-b. After trapping with standard electrophiles, the expected products 15a-c and 17a-b are obtained in 81-98% yield (entries 10-14 of Table 1).

The metalation of pyrimidine derivatives is a challenging problem due to the propensity of these heterocycles to add organometallic reagents.[8] The inventors found that the inverse addition of the pyrimidine derivatives 18-20 to a THF solution of 5b (1.05 equiv.) at −55° C. for approx. 5 min. provides the corresponding magnesiated derivatives 21-23 in 83-90% yields as indicated by iodolysis experiments leading to the iodinated pyrimidines 24-26 (scheme 3).

The mixed magnesium-lithium amide 5b is also well suited for the regioselective metalation of polyfunctional aromatic systems. Thus, the reaction of 2-phenylpyridine 27 in THF at 55° C. with 5b (2.0 equiv.) for 24 h provides the Grignard reagent 28 showing a rare case where a phenyl ring is preferentially metalated compared to a pyridine ring. After iodolysis, the ortho-iodinated product 29 is obtained in 80% yield. Interestingly, the metalation of polyfunctional aromatics such as the bromodiester 30 also succeeds using only the stoichiometric amount of base 5b (1.1 equiv.) in THF (−30° C., 0.5 h) leading regioselectively to the arylmagnesium species 31 which after iodolysis furnishes the polyfunctional aromatic derivative 32 in 88% yield.

Scheme 4. Regioselective magnesiation of polyfunctional aromatic systems

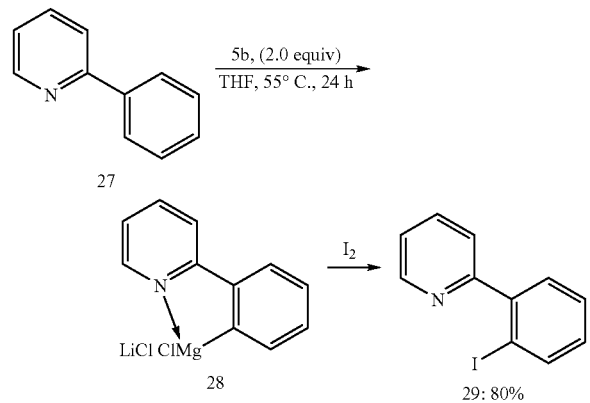

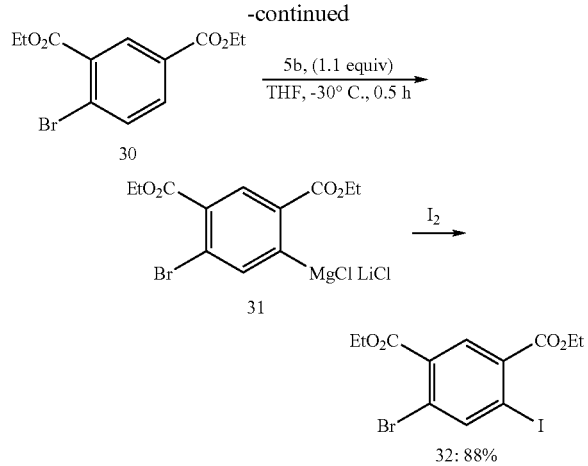

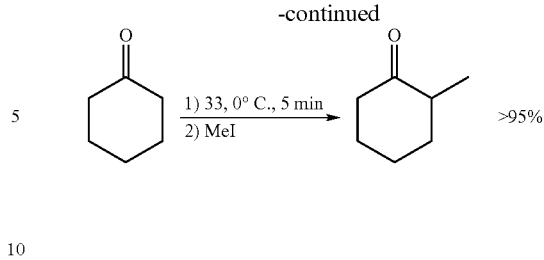

The Grignard reagents can also be used to prepare a polymeric base. 2,2,6,6-tetramethyl piperidine (TMPH) is a well known base. It can be used to prepare the corresponding mixed Mg/Li amide TMPMgCl.LiCl 5b. This monomeric base is very reactive but also very expensive. A corresponding polymeric base to TMPH is CHIMASSORB® 994 (N,N'-bis(2,2,6,6-tetramethylpiperidin-4-yl)hexane-1,6-diamine; 2,4,6-trichloro-1,3,5-triazine; 2,4,4-trimethylpentan-2-amine), the structure of which is shown in Scheme 6.

Scheme 6: Structure of CHIMASSORB® 994

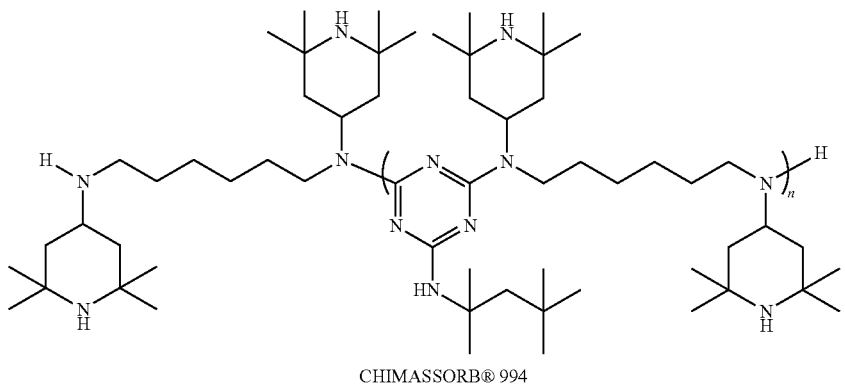

A solution of TMPMgCl LiCl can easily be prepared in THF due to its excellent solubility and it is stable for more than 6 months at 25° C. The use of TMPMgCl LiCl allows for the regioselective functionalization of various aromatics and heteroaromatics. It gives access to new magnesium species not readily available via a Br/Mg-exchange reactions or by previously reported metalation procedures.

The residues $R^1$ and $R^2$ are not limited to organic compounds. $R^1$ and $R^2$ may also be silylated compounds like trimethylsilyl. The preparation of the bis(trimethylsilyl)amide 33 can be achieved by reacting bis(trimethylsilyl)amine with i-PrMgCl LiCl at room temperature (see Scheme 5). This base can efficiently be used to deprotonate ketones like e.g. cyclohexanone as can be seen from Scheme 5.

CHIMASSORB® 994 can be used to prepare the corresponding mixed Mg/Li amide by reacting CHIMASSORB® 994 with i-PrMgCl.LiCl at room temperature (see Scheme 5). This base 34 is stable and soluble in THF before and after deprotonation. As being a polymeric base, it can be easily removed after completion of the reaction. Since CHIMASSORB® 994 is much cheaper than TMP, a corresponding base can be prepared at reduced costs. The polymeric base 34 shows slightly lower activity than monomeric TMPMgCl.LiCl but is nevertheless very effective in deprotonating compounds with acidic protons like isoquinoline. A corresponding example is shown in Scheme 7. The polymeric base can be used to deprotonate various substrates. For example, isoquinoline reacts at room temperature with the base 34 affording after quenching with iodine 1-iodoisoquinoline 7a.

Scheme 7: Preparation and use of the mixed Mg/Li amide of CHIMASSORB® 994

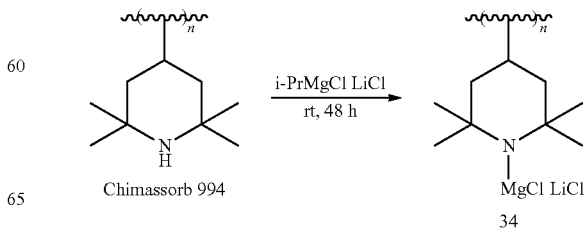

Scheme 5: Preparation and use of silylated magnesium amide

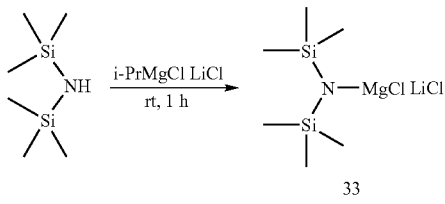

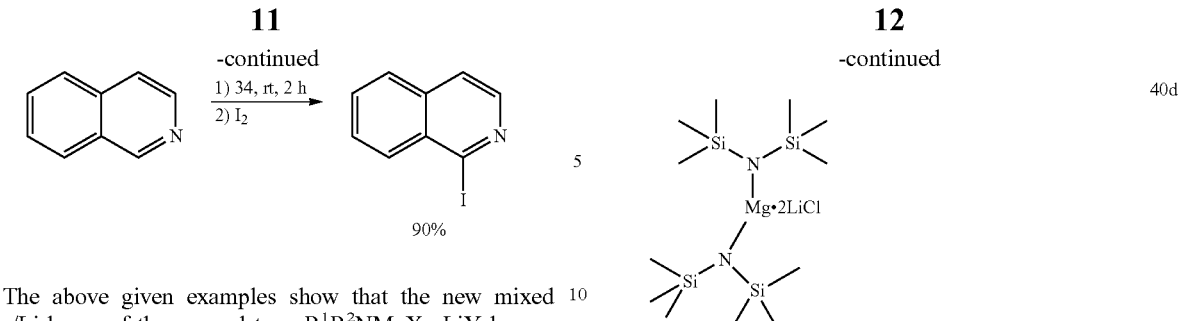

The above given examples show that the new mixed Mg/Li-bases of the general type $R^1R^2NMgX \cdot zLiY$ have a high kinetic activity due to the presence of a lithium salt which breaks oligomeric aggregates of magnesium amides.

An example of a symmetrical bisamide reagent is $(TMP)_2Mg \cdot 2LiCl$ 40a. It is prepared by reacting in situ generated $MgCl_2$ with lithium 2,2,6,6-tetramethylpiperidide (TMPLi) in THF at 0° C. for 30 minutes (see Scheme 8).

Scheme 8: Preparation of the bisamide $(TMP)_2Mg \cdot 2LiCl$ (40a).

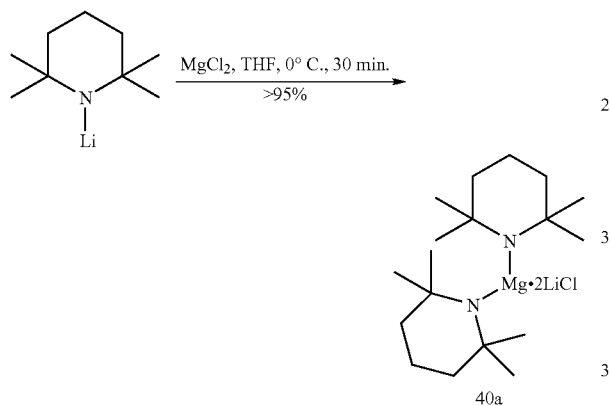

Additionally, other symmetrical bisamides can be prepared in high yields using the same methodology as for the preparation of 40a. All examples shown below (40b-40c) were prepared in >95% yield (Scheme 9) in analogy to the preparation of 40a. This also includes bisamides containing silyl substituted amines.

Scheme 9: Further examples of symmetrical bisamides.

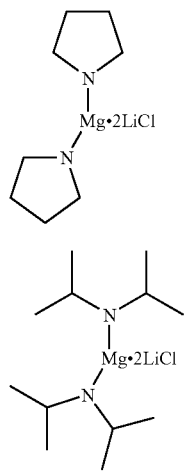

Comparative metalation experiments on aromatic substrates were performed under identical conditions with 1.1 equivalents of both $(TMP)_2Mg \cdot 2LiCl$ (40a) and $TMPMgCl \cdot LiCl$ (5b). The bisamide reagent $(TMP)_2Mg \cdot 2LiCl$ shows highly superior reactivity than $TMPMgCl \cdot LiCl$ and it was even able to deprotonate very weak acidic substrates.

Scheme 10 gives an overview over examples of reactions of four different aromatic substances (41-44) with $(TMP)_2Mg \cdot 2LiCl$ (40a) and $TMPMgCl \cdot LiCl$ (5b) under identical conditions. The respective yields are indicated for the products of each of the two amides 40a and 5b. This experiment clearly shows the even superior reactivity of the bisamides in view of the monoamides. All reactions are carried out at room temperature (rt) being at 25° C.

Scheme 10: Comparison of reaction of aryls with monoamide 5b and bisamide 40a.

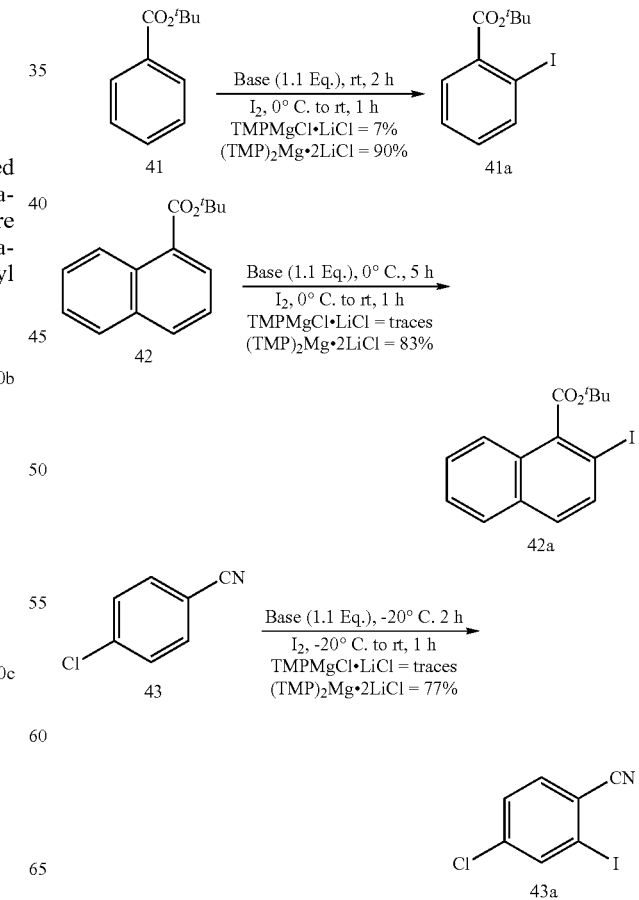

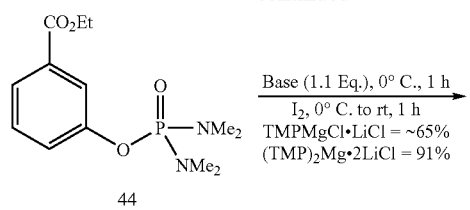

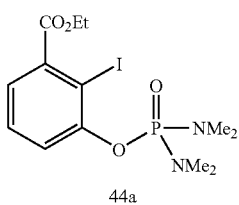

Additionally, the resultant Grignard intermediates derived from (TMP)₂Mg.2LiCl show good stability and tolerance to various substrates. Furthermore, they react with different eletrophiles providing the corresponding functionalized derivatives in good yields. Examples are shown in Table 2 below.

It could also be shown that mixed magnesium bases bearing two different amide functions, i.e. R¹R²N and R³R⁴N being different, have improved properties over the corresponding symmetrical reagents bearing two identical amide functions. The unsymmetrical reagents 40e-40i are prepared from TMPMgCl.LiCl, i-Pr₂NMgCl.LiCl and (2-ethylhexyl)₂NMgCl.LiCl[9], respectively, and the corresponding lithium species of 1H-benzotriazole (Bt), 5,6-dimethyl-1H-benzotriazole (DMBt) and carbazole (CBZ), respectively (Scheme 11).

Especially, the base 40e provides a far higher reactivity than TMPMgCl.LiCl (5b) and (TMP)₂Mg.2LiCl (40a) when using special directing metalation groups (DMG). TMPMgCl.LiCl provides full metalation of 44 in 90 minutes at 0° C., and reagent 40a provides full metalation in 60 minutes. In contrast thereto, the use of 40e provides full metalation at 0° C. in only 10 minutes. Furthermore, only 1.3 equivalents of the base 40e are used in contrast to 1.5 equivalents of TMPMgCl.LiCl. Moreover, the yield of 45a is higher compared to the use of TMPMgCl.LiCl (Scheme 12).

Scheme 11: Preparation of compound 40e-40i having two different amide functions.

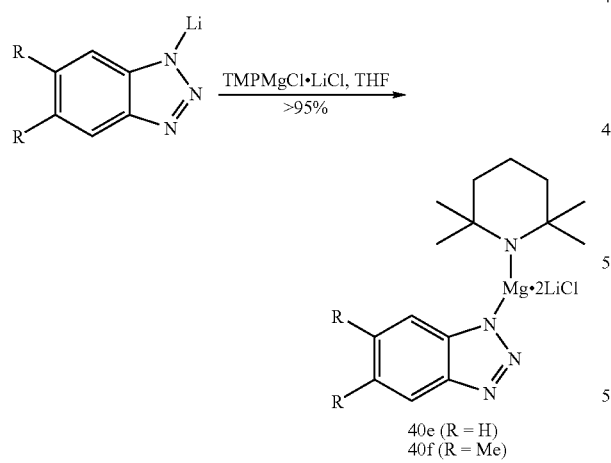

Scheme 12: Comparison of the reactivity of unsymmetrical bisamide 40e in view of monoamide 5b and symmetrical bisamide 40a.

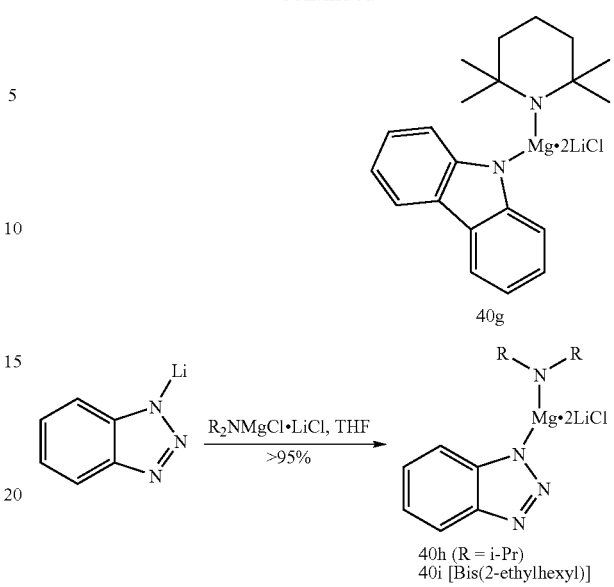

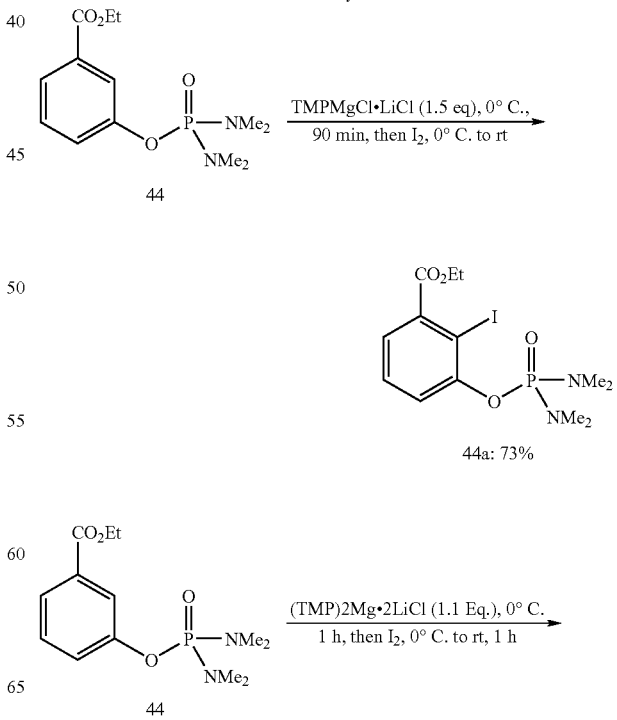

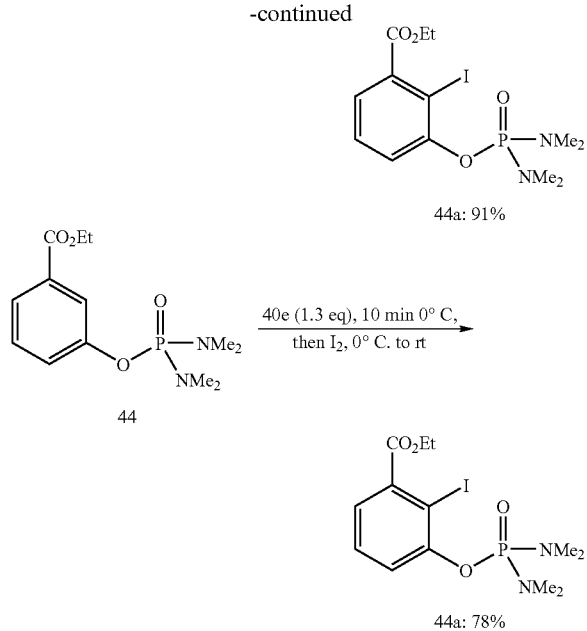

44a: 91%

44a: 78%

The regulating intermediates derived from (TMP)Mg(Bt).2LiCl show good stability and tolerance to various substrates. They can be trapped with an electrophile like iodine to provide the corresponding functionalized derivatives in good yields. Examples are shown in Table 3.

As can be seen from the above given examples, the new mixed Mg/Li-bases are very effective in deprotonating organic compounds. The deprotonation can be achieved in different solvents and can preferably be conducted at temperatures between −90° C. and 100° C. Further, due to the effective deprotonation reaction, the amides of the present invention preferably only require the use of 0.9-5 equivalents, more preferably 1-2 equivalents and most preferably 1.1-1.5 equivalents per proton to be deprotonated.

With this new type of base, which is highly soluble and the side products of which do not disturb the following reactions, many new products may be obtained, or known reactions pathways will be more efficient. A person skilled in the art will easily recognise the benefit of the new Mg/Li-base and will be able to use this base in a wide variety of chemical reactions.

In the following, examples are given to illustrate the present invention. However, these examples are given for illustrative purposes only and are not supposed to limit the scope of the invention which is determined by the claims below.

Experimental Section:

Preparation of the reagent TMPMgCl LiCl (5b):

A dry and argon flushed 250 mL flask, equipped with a magnetic stirrer and a septum, was charged with freshly titrated i-PrMgCl LiCl (100 mL, 1.2 M in THF, 120 mmol). 2,2,6,6-tetramethylpiperidine (TMPH) (19.8 g, 126 mmol, 1.05 equiv) was added dropwise at room temperature. The reaction mixture was stirred until gas evaluation was completed (ca. 24 h) at room temperature.

Preparation of 1-iodoisoquinoline (7a):

A dry and argon flushed 10 mL flask, equipped with a magnetic stirrer and a septum, was charged with TMPMgCl LiCl (5 mL, 1.2 M in THF, 6.0 mmol). Isoquinoline (703 mg, 5.45 mmol) in THF (5 ml) was added dropwise at room temperature. During addition, the reaction mixture became red and the metalation was complete after 2 h (as checked by GC analysis of reaction aliquots quenched with a solution of $I_2$ in THF, the conversion was more than 98%). A solution of $I_2$ in THF (6 ml, 1 M in THF, 6.0 mmol) was slowly added at −20° C. The reaction mixture was quenched with sat. aqueous $NH_4Cl$ solution (10 mL). The aqueous phase was extracted with ether (4×10 mL), dried with $Na_2SO_4$ and concentrated in vacuo. The crude residue was purified by filter column chromatography ($CH_2Cl_2$/pentane) yielding 1-iodoisoquinoline (7a; 1.33 mg, 96%) as slightly yellow crystals (mp=74-76° C.).

The products listed in table 1 below can be produced according to the preparation of 1-iodoisoquinoline (7a).

TABLE 1

Products obtained by the magnesiation of heterocycles with TMPMgCl LiCl (5b) and reaction with electrophiles.

| Entry | Magnesium reagent[a] | T, t [° C., h][b] | Electophile | Product | Yield (%)[c] |
|---|---|---|---|---|---|
| 1 | 6 | 25, 2 | $I_2$ | 7a: R = I | 96 |
| 2 | 6 | 25, 2 | PhCOCl[d] | 7b: R = COPh | 86 |
| 3 | 6 | 25, 2 | I—C₆H₄—CO₂Et | 7c: R = 4-EtO₂C₆H₄ | 82 |
| 4 | 8 | −30, 0.5 | $I_2$ | 40: R = I | 96 |

TABLE 1-continued

Products obtained by the magnesiation of heterocycles with TMPMgCl·LiCl (5b) and reaction with electrophiles.

| Entry | Magnesium reagent[a] | T, t [° C., h][b] | Electophile | Product | Yield (%)[c] |
|---|---|---|---|---|---|
| 5 | 8 | −30, 0.5 | DMF | 9b: R = CHO | 93 |
| 6 | 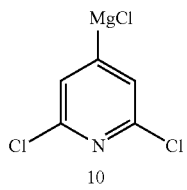 10 | 25, 0.1 | I₂ | 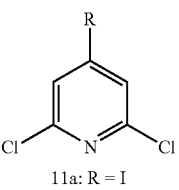 11a: R = I | 93 |
| 7 | 10 | 25, 0.1 | DMF | 11b: R = CHO | 90 |
| 8 | 10 | 25, 0.1 | PhCHO | 11c: R = CH(OH)Ph | 84 |
| 9 | 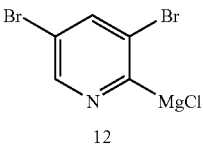 12 | −25, 0.5 | DMF | 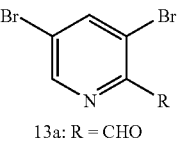 13a: R = CHO | 95 |
| 10 | 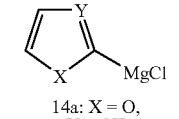 14a: X = O, Y = CH | 25, 24 | DMF | 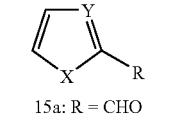 15a: R = CHO | 81 |
| 11 | 14b: X = S, Y = CH | 25, 24 | DMF | 15b: R = CHO | 90 |
| 12 | 14c: X = S, Y = N | 0, 0.1 | PhCHO | 15c: R = CH(OH)Ph | 94 |
| 13 | 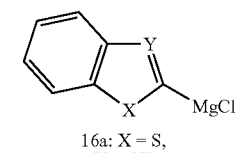 16a: X = S, Y = CH | 25, 24 | DMF | 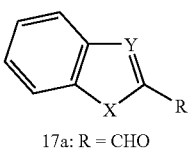 17a: R = CHO | 93 |
| 14 | 16b: X = S, Y = N | 0, 0.1 | I₂ | 17b: R = I | 98 |

[a]Lithium chloride and TMPH are complexed to the Grignard reagent.
[b]Reaction conditions for the deprotonation with TMPMgCl·LiCl (5b, 1.1 equiv.).
[c]Isolated yield of analytically pure product.
[d]A transmetalation with CuCN·2LiCl (0.2 equiv) was performed Preparation of (TMP)₂Mg·2LiCl (40a).

Magnesium turnings (15 mmol) were placed in an argon-flushed-Schlenk flask and THF (30 ml) was added. 1,2-Dichloroethane (16 mmol) was added dropwise and the reaction was stirred until all magnesium was consumed, approximately 2 h. In another argon-flushed-Schlenk flask 2,2,6,6-tetramethylpiperidine (TMPH) (30 mmol) and THF (20 ml) were placed. This solution was cooled to 40° C. and n-BuLi (30 mmol) was added dropwise. After the addition, the reaction mixture was warmed to 0° C. and stirred at same temperature for 30 min. The MgCl₂ solution was then transferred via cannula into the TMPLi solution and the reaction mixture was stirred at 0° C. for 30 min, then warmed to room temperature and stirred for an additional 1 h. The solvents were removed then in vacuo followed by addition of THF while stirring until complete dissolution of the salts. The fresh (TMP)₂Mg·2LiCl solution was titrated prior to use at 0° C. against benzoic acid using 4-(phenylazo)-diphenylamine as indicator. Average concentration in THF was 0.6 mol/l.

Preparation of (PIR)₂Mg·2LiCl (40b).

Prepared according to 40a from pyrrolidine (PIR) (30 mmol), n-BuLi (30 mmol), magnesium turnings (15 mmol) and 1,2-dichloroethane (16 mmol) in THF. Average concentration in THF was found to be 0.65 mol/l.

Preparation of (i-Pr)₂NMg·2LiCl (40c).

Prepared according to 40a from diisopropylamine (30 mmol), n-BuLi (30 mmol), magnesium turnings (15 mmol) and 1,2-dichloroethane (16 mmol) in THF. Average concentration in THF was found to be 0.84 mol/l.

Preparation of (HMDS)₂Mg·2LiCl (40d).

Prepared according to 40a from 1,1,1,3,3,3-hexamethyldisilazane (HMDS) (30 mmol), n-BuLi (30 mmol), magnesium turnings (15 mmol) and 1,2-dichloroethane (16 mmol) in THF. Average concentration in THF was found to be 0.86 mol/L.

Magnesiations of functionalized arenes with (TMP)$_2$Mg.2LiCl

Preparation of di-tert-butyl 4-iodobenzene-1,3-dioate (51a)

A dry and nitrogen-flushed 10-ml-Schlenk-flask, equipped with a magnetic stirring bar and a septum, was charged with a solution of the di-tert-butyl isophthalate (278 mg, 1 mmol) in dry THF (1 ml). After cooling to 0° C., a freshly prepared (TMP)$_2$Mg.2LiCl solution (0.6 mol/l in THF, 1.83 ml, 1.1 mmol) was added dropwise and the reaction mixture was stirred at the same temperature. The completion of the metalation (2 h) was checked by GC-analysis of reaction aliquots quenched with a solution of I$_2$ in dry ether. Iodine (508 mg, 2 mmol) dissolved in dry THF (2 ml) was then added at 0° C. and the resulting mixture warmed to room temperature. After stirring for 1 hour, the reaction mixture was quenched with sat. aq. Na$_2$S$_2$O$_3$, extracted with ether (3×20 ml) and dried over Na$_2$SO$_4$. After filtration the solvent was removed in vacuo. Purification by flash-chromatography (n-pentane/diethyl ether, 10:1) furnished compound 51a (380 mg, 94%) as a yellow oil.

The products listed in Table 2 below can be produced according to the preparation of di-tert-butyl 4-iodobenzene-1,3-dioate (51a), using the corresponding temperatures and reactions times as indicated in the table.

TABLE 2

Products obtained by the magnesiation of aromatics with (TMP)$_2$Mg2LiCl and reactions with eletrophiles.

| Entry | Substrate | Temp. [° C.] | Time | Electrophile E⁻ | Product | Yield |
|---|---|---|---|---|---|---|
| 1 | 41 (CO$_2$t-Bu-phenyl) | 25 | 1 h | PhCOCl[a] | 41b: E = COPh | 93% |
| 2 | 41 | 25 | 1 h | p-IPhCO$_2$Et[b] | 41c: E = p-PhCO$_2$Et | 82% |
| 3 | 53 (Br, CO$_2$t-Bu) | −10 | 1 h | I$_2$ | 53a: E = I | 71% |
| 4 | 53 | −10 | 1 h | PhCOCl[a] | 53b: E = COPh | 52% |
| 5 | 45 (CO$_2$i-Pr-phenyl) | 25 | 1 h | I$_2$ | 45a: E = I | 78% |
| 6 | 45 | 25 | 1 h | EtCOCl[a] | 45b: E = COEt | 7% |
| 7 | 46: X = H (CN) | 0 | 2 h | I$_2$ | 46a: E = I | 6% |
| 8 | 47: X = Br | −20 | 3 h | I$_2$ | 47a: E = I | 74% |
| 9 | 48 (Ph-CO-, OBoc) | −20 | 4 h | I$_2$ | 48a: E = I | 91% |
| 10 | 48 | −20 | 4 h | PhCOCl[a] | 48b: E = PhCO | 62% |

TABLE 2-continued

Products obtained by the magnesiation of aromatics with (TMP)₂Mg2LiCl and reactions with eletrophiles.

| Entry | Substrate | Temp. [° C.] | Time | Electrophile E⁻ | Product | Yield |
|---|---|---|---|---|---|---|
| 11 | 42 (1-CO₂Et naphthalene) | 0 | 5 h | BrCl₂C₂Cl₂Br | 42b: E = Br | 60% |
| 12 | 49 (3,5-bis(CO₂Et)pyridine) | −40 | 5 h | I₂ | 49a: E = I | 77% |
| 13 | 49 | −40 | 5 h | BrCl₂C₂Cl₂Br | 49b: E = Br | 70% |
| 14 | 50 (4-CO₂Et pyridine) | −40 | 12 h | I₂ | 50a: E = I | 66% |
| 15 | 51 (1,3-bis(CO₂t-Bu)benzene) | 25 | 2 h | I₂ | 51a: E = I | 94% |

[a]A transmetalation with CuCN·2LiCl was performed.
[b]Obtained by palladium-catalyzed cross-coupling after transmetalation with ZnCl₂.

Preparation of (TMP)Mg(Bt).2LiCl (40e):

Benzotriazole (Bt) (1.19 g, 10.0 mmol) was placed in a flame dried, argon flushed 50 ml Schlenk tube equipped with magnetic stirring bar and septum. THF (10 ml) was added. The solution was cooled to −40° C. Then n-BuLi (3.62 ml, 2.76 M in hexane, 10.0 mmol) was added drop wise. White precipitate was formed immediately. After the end of the addition the resulting suspension was stirred at −40° C. for 30 min. Then solvents were removed in vacuo followed by addition of TMPMgCl.LiCl (8.93 ml, 1.12 M in THF, 10.0 mmol). After the complete dissolving of the white solid, THF was removed in vacuo. To the resulting brownish gel, THF was added while stirring until complete dissolution of the salts. The fresh (TMP)Mg(Bt).2LiCl solution was titrated at room temperature against benzoic acid using 4-(phenylazo)-diphenylamine as an indicator. Average concentration in THF was found to be 0.35 mol/l.

Preparation of (TMP)Mg(DMBt).2LiCl (40f):

Prepared according to 40e from 5,6-dimethyl-1H-benzotriazole (10 mmol), n-BuLi (10 mmol) and TMPMgCl.LiCl (10 mmol) in THF. Average concentration in THF was found to be 0.33 mol/l.

Preparation of (TMP)Mg(CBZ).2LiCl (40g):

Prepared according to 40e from 9H-carbazole (10 mmol), n-BuLi (10 mmol), TMPMgCl.LiCl (10 mmol) in THF. Average concentration in THF was found to be 0.33 mol/l.

Preparation of (i-Pr₂N)Mg(Bt).2LiCl (40h):

Prepared according to 40e from benzotriazole (10 mmol), n-BuLi (10 mmol) and (i-Pr₂N)MgCl.LiCl (10 mmol) in THF. Average concentration in THF was found to be 0.24 mol/l.

Preparation of (2-ethyl-hexyl)₂NMg(Bt).2LiCl (40i):

Prepared according to 40e from benzotriazole (10 mmol), n-BuLi (10 mmol) and (2-ethyl-hexyl)₂NMgCl LiCl (10 mmol) in THF. Average concentration in THF was found to be 0.23 mol/l.

Magnesiations of Functionalized Arenes with (TMP)Mg(Bt).2LiCl

Preparation of ethyl 3-{[bis(dimethylamino)phosphoryl]oxy}-2-iodobenzoate (44a)

A dry and nitrogen-flushed 25-ml Schlenk flask, equipped with a magnetic stirring bar and a septum, was charged ethyl 3-{[bis(dimethylamino)phosphoryl]oxy}benzoate 44 (300 mg, 1.00 mmol) in dry THF (3 ml). After cooling to 0° C., a freshly prepared (TMP)Mg(Bt).2LiCl solution (4.33 ml, 0.3 M in THF, 1.3 mmol) was added dropwise and the reaction mixture was stirred at the same temperature. The completion of the metalation (10 min) was checked by GC-analysis of reaction aliquots quenched with a solution of I₂ in dry THF. Iodine (508 mg, 2.0 mmol) dissolved in dry THF (2 ml) was then added at 0° C. and the resulting mixture warmed to room temperature. After stirring for 1 hour, the reaction mixture was quenched with sat. aq. $Na_2S_2O_3$, extracted with ether (3×20 ml) and dried over $Na_2SO_4$. After filtration, the solvent was removed in vacuo. Purification by flash-chromatography using ethyl acetate as eluent furnished ethyl 3-{[bis(dimethylamino)phosphoryl]oxy}-2-iodobenzoate 44a (332 mg, 78%) as a yellow oil.

The products listed in Table 3 below can be produced according to the preparation of ethyl 3-{[bis(dimethylamino)phosphoryl]oxy}-2-iodobenzoate 44a, using the corresponding temperatures and reactions times as indicated in the table.

TABLE 3

Products obtained by the magnesiation of aromatics with (TMP)Mg(Bt)·2LiCl and reactions with eletrophiles.

| Entry | Substate | Temp. [° C.] | Time | Electrophile | Product | Yield |
|---|---|---|---|---|---|---|
| 1 | 41 (CO₂t-Bu phenyl) | 0 | 6 h | $I_2$ | 41a (2-iodo CO₂t-Bu phenyl) | 69% |
| 2 | 41 | 25 | 1 h | $I_2$ | 41a | 67% |
| 3 | 44 | 0 | 10 min | $I_2$ | 44a | 78% |
| 4 | 52 | 0 | 30 min | $I_2$ | 52a | 73% |

REFERENCES AND NOTES

[1] a) M. Schlosser, *Angew. Chem. Int. Ed.* 2005, 44, 376-393. b) A. Turck, N. Ple, F. Mongin, G. Quéguiner, *Tetrahedron* 2001, 57, 4489-4505. c) F. Mongin, G. Quéguiner, *Tetrahedron* 2001, 57, 4059-4090 d) M. Schlosser, *Eur. J. Org. Chem.* 2001, 21, 3975-3984. e) D. M. Hodgson, C. D. Bray, N. D. Kindon, *Org. Lett.* 2005, 7, 2305-2308. f) J-C. Plaquevent, T. Perrard, D. Cahard, *Chem. Eur. J.* 2002, 8, 3300-3307. g) C.-C. Chang, M. S. Ameerunisha, *Coord. Chem. Rev.* 1999, 189, 199-278. h) J. Clayden, *Organolithiums: Selectivity for Synthesis.* Editor(s): J. E. Baldwin, R. M. Williams 2002, Publisher: Elsevier. i) F. Leroux, M. Schlosser, E. Zohar, I. Marek, *The preparation of organolithium reagents and intermediates* Editor(s): Rappoport, Zvi; Marek, Ilan. *Chemistry of Organolithium Compounds* 2004, 1, 435-493. Publisher: John Wiley & Sons Ltd. j) K. W. Henderson, W. J. Kerr, *Chem.-A Eur. J.* 2001, 7(16), 3430-3437. k) K. W. Henderson, W. J. Kerr, J. H. Moir, *Tetrahedron* 2002, 58(23), 4573-4587.1) M. C. Whisler, S. MacNeil, V. Snieckus, P. Beak, *Angew. Chem. Int. Ed.* 2004, 43(17), 2206-2225. m) G. Queguiner, F. Marsais, V. Snieckus, J. Epsztajn, *Adv. in Het. Chem.* 1991, 52, 187-304. n) M. Veith, S. Wieczorek, K. Fries, V. Huch, *Z. Anorg. Allg. Chem.* 2000, 626(5), 1237-1245.

[2] a) M-X. Zhang, P. E. Eaton, *Angew. Chem. Int. Ed.* 2002, 41, 2169-2171. b) Y. Kondo, Y. Akihiro, T. Sakamoto, *J. Chem. Soc., Perkin Trans. 1: Org. Bio-Org. Chem.* 1996, 19, 2331-2332. c) P. E. Eaton, C. H. Lee, Y. Xiong, *J. Am. Chem. Soc.* 1989, 111, 8016-18. d) P. E. Eaton, M-X. Zhang, N. Komiya, C-G. Yang, I. Steele, R. Gilardi, *Synlett* 2003, 9, 1275-1278. e) P. E. Eaton, R. M. Martin, *J. Org. Chem.* 1988, 53, 2728-32. f) M. Shilai, Y. Kondo, T. Sakamoto, *J. Chem. Soc., Perkin Trans. 1: Org. Bio-Org. Chem.* 2001, 4, 442. g) P. Knochel, W. Dohle, N. Gommermann, F. F. Kneisel, F. Kopp, T. Korn, I. Sapountzis, V. A. Vu, *Angew. Chem.* 2003, 115, 4438-4456.

[3] a) Y. Kondo, M. Shilai, M. Uchiyama, T. Sakamoto, *J. Am. Chem. Soc.* 1999, 121, 3539-3540. b) T. Imahori, M. Uchiyama, T. Sakamoto, Y. Kondo, *Chem. Comm.* 2001, 23, 2450-2451.

[4] A. Krasovskiy, P. Knochel, *Angew. Chem.* 2004, 116, 4438; *Angew. Chem. Int. Ed.* 2004, 43, 3333 b) H. Ren, A. Krasovskiy, P. Knochel, *Chem. Commun.* 2005, 543. c) H. Ren, A. Krasovskiy, P. Knochel, *Org. Lett.* 2004, 6, 4215.

[5] i-PrMgCl LiCl is commercially available from Chemetall GmbH (Frankfurt)

[6] a) A. J. Clarke, S. McNamara, O. Meth-Cohn, *Tetrahedron Lett.* 1974, 27, 2373-6. b) Y. G. Gu; E. K. Bayburt, *Tetrahedron Lett.* 1996, 37, 2565.

[7] a) H. Froehlich, W. Kalt, *J. Org. Chem.* 1990, 55, 2993-5. b) C. Peyron, J-M. Navarre, N. Van Craynest, R. Benhida, *Tetrahedron Lett.* 2005, 46, 3315-3318. c) D. W. Slocum, P. L. Gierer, *J. Org. Chem.* 1976, 41, 3668-74.

[8] a) Y. G. Gu, E. K. Bayburt, *Tetrahedron Lett.* 1996, 37, 2565-8. b) W. Schlecker, A. Huth, E. Ottow, J. Mulzer, *Lieb. Ann.* 1995, 8, 1441-6. c) W. Schlecker, A. Huth, E. Ottow, J. Mulzer, *J. Org. Chem.* 1995, 60, 8414-16. d) A. Bouillon, J-C. Lancelot, V. Collot, P. R. Bovy, S. Rault, *Tetrahedron* 2002, 58, 3323-3328. e) A. Bouillon, J-C. Lancelot, J. S. de O, Santos, V. Collot, P. R. Bovy, S. Rault, *Tetrahedron* 2003, 59, 10043-10049. f) A. Bouillon, J-C. Lancelot, V. Collot, P. R. Bovy, S. Rault, *Tetrahedron* 2002, 58, 4369-4373. g) A. Bouillon, J-C. Lancelot, V. Collot, P. R. Bovy, S. Rault, *Tetrahedron* 2002, 58, 2885-2890. h) H. Awad, F. Mongin, F. Trecourt, G. Queguiner, F. Marsais, *Tetrahedron Lett.* 2004, 45, 7873-7877. i) D. L. Comins, M. O. Killpack, *J. Org. Chem.* 1990, 55, 69-73. j) R. Radinov, Kh. Chanev, M. Khaimova, *J. Org. Chem.* 1991, 56, 4793-6. k) S. Choppin, P. Gros, Y. Fort, *Org. Lett.* 2000, 2, 803-805.

[9] (2-Ethyl-hexyl)$_2$NMgCl LiCl is prepared by reacting bis (2-ethylhexyl)amine with i-Pr$_2$NMgCl.LiCl in THF at room temperature for 48 h. For a general procedure see A. Krasovskiy, V. Krasovskaya, P. Knochel, *Angew. Chem. Int. Ed.* 2006, 45, 2958-2961.

The invention claimed is:

1. A reagent of the general formula

wherein

R$^1$ and R$^2$ are, independently, selected from H, substituted or unsubstituted aryl or heteroaryl containing one or more heteroatoms, linear, branched or cyclic, substituted or unsubstituted alkyl, alkenyl, alkynyl, or silyl derivatives thereof; and R$^1$ and R$^2$ together can be part of a cyclic structure; and wherein at least one of R$^1$ and R$^2$ is other than H;

X and Y are, independently, selected from the group consisting of F; Cl; Br; I; CN; SCR NCO; HalO$_n$, wherein n=3 or 4 and Hal is selected from Cl, Br and I; NO$_3$; BF$_4$; PF$_6$; H; a carboxylate of the general formula R$^X$CO$_2$; an alcoholate of the general formula OR$^X$; a thiolate of the general formula SR$^X$; R$^X$P(O)O$_2$; or SCOR$^X$; or SCSR$^X$; O$_n$SR$^X$, wherein n=2 or 3; or NO$_n$, wherein n=2 or 3;

wherein R$^X$ is a substituted or unsubstituted aryl or heteroaryl containing one or more heteroatoms, linear, branched or cyclic, substituted or unsubstituted alkyl, alkenyl, alkynyl, or H;

z>0;

or as adduct with a solvent.

2. Solution of the reagent according to claim 1 in a solvent.

3. Solution according to claim 2, wherein the solvent is selected from cyclic, linear or branched mono or polyethers, thioethers, amines, phosphines, dioxanes, triethylamine, ethyldiisopropylamine, dimethylsulfide, dibutylsulfide; cyclic amides; cyclic, linear or branched alkanes and/or alkenes wherein one or more hydrogens are replaced by a halogen; ureas; aromatic, heteroaromatic or aliphatic hydrocarbons; hexamethylphosphorus triamide (HMPA), CS$_2$; and combinations thereof.

4. A method of deprotonating a substrate, wherein the method comprises reacting the substrate with a reagent of claim 1 and wherein the substrate can form a stabilized or unstabilized carbanion.

5. Process for the preparation of a reagent having the general formula

wherein

R$^1$ and R$^2$ are, independently, selected from H, substituted or unsubstituted aryl or heteroaryl containing one or more heteroatoms, linear, branched or cyclic, substituted or unsubstituted alkyl, alkenyl, alkynyl, or silicon derivatives thereof; and R$^1$ and R$^2$ together can be part of a cyclic structure; and wherein at least one of R$^1$ and R$^2$ is other than H;

X and Y are, independently, selected from the group consisting of F; Cl; Br; I; CN; SCN; NCO; HalO$_n$, wherein n=3 or 4 and Hal is selected from Cl, Br and I; NO$_3$; BF$_4$, PF$_6$; H; a carboxylate of the general formula R$^X$CO$_2$; an alcoholate of the general formula OR$^X$; a thiolate of the general formula SR$^X$; R$^X$P(O)O$_2$; or SCOR$^X$; or SCSR$^X$; O$_n$SR$^X$, wherein n=2 or 3; or NO$_n$, wherein n=2 or 3;

wherein R$^X$ is a substituted or unsubstituted aryl or heteroaryl containing one or more heteroatoms, linear, branched or cyclic, substituted or unsubstituted alkyl, alkenyl, alkynyl, or H; and z>0;

comprising reacting in a solvent R$^1$R$^2$NH with a Grignard reagent R'MgX in the presence of LiY or with R'MgX.zLiY; and wherein R' is selected from substituted or unsubstituted aryl or heteroaryl containing one or more heteroatoms, linear, branched or cyclic, substituted or unsubstituted alkyl, alkenyl, or alkynyl.

6. Process according to claim 5, wherein X and Y are independently or both Cl, Br or I.

7. Process according to claim 5 or 6, wherein z is in the range from 0.01-5.

8. Process according to claim 5, wherein the Grignard reagent R'MgX.zLiY is iPrMgCl.LiCl.

9. Process according to claim 5, wherein the solvent is selected from cyclic, linear or branched mono or polyethers, thioethers, amines, phosphines, dioxanes, triethylamine, ethyldiisopropylamine, dimethylsulfide, dibutylsulfide; cyclic amides; cyclic, linear or branched alkanes and/or alkenes wherein one or more hydrogens are replaced by a halogen; ureas; aromatic, heteroaromatic or aliphatic hydrocarbons; hexamethylphosphorus triamide (HMPA), CS$_2$; and combinations thereof.

10. The reagent of claim 1, wherein R$_1$ and R$_2$ are alkylsilyl.

11. The process of claim 5, wherein R$_1$ and R$_2$ are alkylsilyl.

12. The solution of claim 3, wherein the cyclic, linear or branched mono or polyether is tetrahydrofuran (THF), 2-methyltetrahydrofuran, dibutyl ether, diethyl ether, tert-butylmethyl ether, dimethoxyethane, or a combination thereof.

13. The solution of claim 3, wherein the dioxane is 1,4-dioxane.

14. The solution of claim 3, wherein the cyclic amide is N-methyl-2-pyrrolidone (NMP), N-ethyl-2-pyrrolidone (NEP), N-butyl-2-pyrrolidone (NBP), and combinations thereof.

15. The solution of claim 3, wherein the alkane wherein one or more hydrogens are replaced by a halogen is dichloromethane, 1,2-dichloroethane, carbon tetrachloride ($CCl_4$), and combinations thereof.

16. The solution of claim 3, wherein the urea is N,N'-dimethylpropyleneurea (DMPU).

17. The solution of claim 3, wherein the aromatic, heteroaromatic or aliphatic hydrocarbon is selected from the group consisting of benzene, toluene, xylene, pyridine, pentane, cyclohexane, hexane, and heptane, and combinations thereof.

18. The process of claim 6, wherein X and Y are independently or both Cl.

19. The process of claim 7, wherein z is in the range from 0.5-2.

20. The process of claim 19, wherein z is in the range from 0.9 to 1.2.

21. The process of claim 20, wherein z is about 1.

22. The process of claim 9, wherein the cyclic, linear or branched mono or polyether is tetrahydrofuran (THF), 2-methyltetrahydrofuran, dibutyl ether, diethyl ether, tert-butylmethyl ether, dimethoxyethane, or a combination thereof.

23. The process of claim 9, wherein the dioxane is 1,4-dioxane.

24. The process of claim 9, wherein the cyclic amide is N-methyl-2-pyrrolidone (NMP), N-ethyl-2-pyrrolidone (NEP), N-butyl-2-pyrrolidone (NBP), and combinations thereof.

25. The process of claim 9, wherein the alkane wherein one or more hydrogens are replaced by a halogen is dichloromethane, 1,2-dichloroethane, carbon tetrachloride ($CCl_4$), and combinations thereof.

26. The process of claim 9, wherein the urea is N,N'-dimethylpropyleneurea (DMPU).

27. The process of claim 9, wherein the aromatic, heteroaromatic or aliphatic hydrocarbon is selected from the group consisting of benzene, toluene, xylene, pyridine, pentane, cyclohexane, hexane, and heptane, and combinations thereof.

* * * * *